(12) United States Patent
Ishida et al.

(10) Patent No.: US 9,079,826 B2
(45) Date of Patent: Jul. 14, 2015

(54) METHOD FOR PRODUCING HIGH-PURITY CERAMIDE

(71) Applicant: Takasago International Corporation, Tokyo (JP)

(72) Inventors: Kenya Ishida, Tokyo (JP); Kenji Yagi, Hiratsuka (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 14/366,883

(22) PCT Filed: Nov. 7, 2012

(86) PCT No.: PCT/JP2012/007122
§ 371 (c)(1),
(2) Date: Jun. 19, 2014

(87) PCT Pub. No.: WO2013/094108
PCT Pub. Date: Jun. 27, 2013

(65) Prior Publication Data
US 2014/0364649 A1 Dec. 11, 2014

(30) Foreign Application Priority Data
Dec. 22, 2011 (JP) .................. 2011-281654

(51) Int. Cl.
| | | |
|---|---|---|
| C07C 231/02 | (2006.01) | |
| C07C 231/22 | (2006.01) | |
| C07C 233/18 | (2006.01) | |
| C07C 231/24 | (2006.01) | |
| C07C 235/08 | (2006.01) | |

(52) U.S. Cl.
CPC ............. *C07C 231/02* (2013.01); *C07C 231/22* (2013.01); *C07C 231/24* (2013.01); *C07C 233/18* (2013.01); *C07C 235/08* (2013.01); *C07B 2200/07* (2013.01)

(58) Field of Classification Search
CPC .. C07C 231/02; C07C 231/22; C07C 231/24; C07C 233/18; C07C 235/08; C07B 2200/07
USPC ......................................... 564/135, 216, 224
See application file for complete search history.

(56) References Cited

U.S. PATENT DOCUMENTS

| | | | |
|---|---|---|---|
| 5,618,706 A | 4/1997 | Casey et al. | |
| 5,831,125 A | 11/1998 | Sakurai et al. | |
| 5,840,940 A | 11/1998 | De Pater et al. | |
| 5,869,711 A | 2/1999 | Philippe et al. | |
| 5,998,668 A | 12/1999 | Sakurai et al. | |
| 2010/0022795 A1 | 1/2010 | Honda et al. | |

FOREIGN PATENT DOCUMENTS

| | | |
|---|---|---|
| JP | 62-207247 | 9/1987 |
| JP | 8-283218 | 10/1996 |
| JP | 10-114732 | 5/1998 |
| WO | 2008041571 A1 | 4/2008 |

OTHER PUBLICATIONS

International Preliminary Report on Patentability for corresponding International Application Serial No. PCT/JP2012/007122, Jul. 3, 2014, 11 pages.

*Primary Examiner* — Shailendra Kumar
(74) *Attorney, Agent, or Firm* — Mintz Levin Cohn Ferris Glovsky and Popeo, P.C.; Peter F. Corless; Christopher R. Cowles

(57) ABSTRACT

Provided is a method for producing an optically active ceramide by an N-acylation (amidation) reaction of an optically active aminodiol, wherein a crude ceramide produced therein is purified by an industrially advantageous process. Namely, provided is a method for producing a high-purity ceramide that has high diastereo purity with high yield. A high-purity ceramide is produced by: a step wherein a ceramide represented by general formula (1) is produced by reacting an aminodiol with an alkyl ester having 1-5 carbon atoms of an aliphatic carboxylic acid having 12-24 carbon atoms, said aliphatic carboxylic acid optionally having a hydroxyl group, in a hydrocarbon solvent having 5-10 carbon atoms; and a step wherein an alcohol having 1-3 carbon atoms is added into the reaction mixture obtained in the preceding step, thereby causing crystals to precipitate.

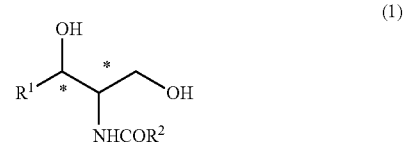

(1)

(In the formula, $R^1$ represents an alkyl group which has 13-17 carbon atoms and optionally has a carbon-carbon unsaturated bond; $R^2$ represents an alkyl group which has 11-23 carbon atoms and optionally has a hydroxyl group; and * represents an optically active state.).

12 Claims, No Drawings

METHOD FOR PRODUCING HIGH-PURITY CERAMIDE

CROSS-REFERENCES TO RELATED APPLICATIONS

This application is a 35 U.S.C. §371 U.S. national entry of International Application PCT/JP2012/007122 (WO 2013/094108) having an International filing date of Nov. 7, 2012, which claims under 35 U.S.C. §119(a) the benefit of Japanese Application No. 2011-281654, filed Dec. 22, 2011, the entire contents of all of which applications are incorporated herein by reference.

TECHNICAL FIELD

The present invention relates to a method for purifying a ceramide.

BACKGROUND ART

A ceramide is constituted of a sphingoid (a long-chain amino alcohol having 16 to 20 carbon atoms) and a fatty acid bonded to each other and a glycosphingolipid is the ceramide bonded with sugar. The glycosphingolipid is a main glycolipid of animals and is a substance which is localized mainly in a cell membrane. Moreover, it is understood that the ceramide is present as a lamella structure in the intercellular lipid of the stratum corneum of the skin, plays an important role as a water permeability barrier of the skin, and is useful for prevention of dry skin or prevention of aging skin (see Patent Document 1).

As a method for producing a ceramide, reported are a method for producing tetraacetyl phytosphingosine (TAPS) by a fermentation method using mutant strains of microorganisms (see Patent Document 1), a method for producing an optically active ceramide by transesterification of carboxylic acid esters in an alcohol solvent such as butanol (see Patent Document 2), and a method for producing N-linoleoylphytosphingosine by amidating linoleic acid and phytosphingosine in ethyl acetate using p-toluenesulfochloride (see Patent Document 3), for example. In addition, it is reported that a ceramide acylated by carboxylic acid having a hydroxyl group can be produced using carboxylic acid ester having a hydroxyl group by a method similar to that described in Patent Document 2 (see Patent Document 4).

In the method described in Patent Document 2, the crude ceramide recovered from the reactor is cooled and then the precipitated crystals are washed and dried with methanol, however, crystal separation efficiency is poor. In addition, since a butanol used as a solvent remains, it is very difficult to remove the butanol and/or butanol odor. Further, in the method described in Patent Document 3, ethyl acetate is used as a solvent and a cumbersome washing procedure needs to be repeated after the reaction. Moreover, the yield is also very low and thus the method is not considered as an industrially advantageous method. In the method described in Patent Document 4, recrystallization is carried out using methanol and thus the method is also not considered as an industrially advantageous method.

As described above, there has not been established yet an industrially advantageous method which enables to produce a ceramide having high purity in large quantities.

CITATION LISTS

Patent Documents

Patent Document 1: U.S. Pat. No. 5,618,706
Patent Document 2: U.S. Pat. No. 5,831,125
Patent Document 3: U.S. Pat. No. 5,840,940
Patent Document 4: U.S. Pat. No. 5,998,668

SUMMARY OF THE INVENTION

Problems to be Solved by the Invention

The present invention is to provide an industrially advantageous method for purifying generated crude ceramide, wherein the method is used in a method for producing an optically active ceramide by an N-acylation (amidation) reaction of an optically active aminodiol, and to provide a method for producing a high-purity ceramide having high diastereomeric purity with high yield.

Means for Solving the Problems

The inventors of the present invention conducted intensive studies in order to solve the above problems. As a result, they found that, when an aliphatic hydrocarbon and an alcohol were used as a solvent, a crude ceramide could be purified and it was possible to obtain a high-purity ceramide having high diastereomeric purity with high yield, with a simple procedure. In addition, they found that, in a process of producing an optically active ceramide by an N-acylation (amidation) reaction of an optically active aminodiol, amidation could be carried out with high yield even when an aliphatic hydrocarbon was used as a solvent. Moreover, they found that, when the N-acylation (amidation) reaction of an optically active aminodiol was carried out using an aliphatic hydrocarbon as a solvent and then an alcohol was added into the reaction mixture to cause crystals to precipitate, it was possible to obtain a high-purity ceramide having high diastereomeric purity with high yield, with a simple procedure.

That is, the present invention relates to a method for producing a high-purity ceramide, the method including a process of dissolving a crude ceramide represented by the following general formula (1) in a hydrocarbon solvent having 5 to 10 carbon atoms and adding an alcohol having 1 to 3 carbon atoms into the solution,

[Chemical Formula 1]

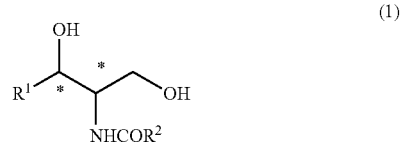

(in the formula, R$^1$ represents an alkyl group having 13 to 17 carbon atoms which optionally has carbon-carbon unsaturated bond(s); R$^2$ represents an alkyl group having 11 to 23 carbon atoms which optionally has hydroxyl group(s); and * indicates an optically active center.).

In addition, the present invention relates to a method for producing a ceramide represented by the above-described general formula (1) by reacting an aminodiol represented by the following general formula (2) with a 1 to 5 carbon atoms of alkyl ester of an aliphatic carboxylic acid having 12 to 24 carbon atoms, wherein the aliphatic carboxylic acid optionally has hydroxyl group(s), in a hydrocarbon solvent having 5 to 10 carbon atoms,

[Chemical Formula 2]

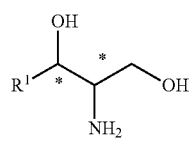
(2)

(in the formula, $R^1$ represents an alkyl group having 13 to 17 carbon atoms which optionally has carbon-carbon unsaturated bond(s); and * indicates an optically active center.).

Further, the present invention relates to a method for producing a high-purity ceramide, the method including a process of reacting an aminodiol represented by the above-described general formula (2) with a 1 to 5 carbon atoms of alkyl ester of an aliphatic carboxylic acid having 12 to 24 carbon atoms, wherein the aliphatic carboxylic acid optionally has hydroxyl group(s), in a hydrocarbon solvent having 5 to 10 carbon atoms, and a process of adding an alcohol having 1 to 3 carbon atoms into the reaction mixture in which a crude ceramide represented by general formula (1) generated in the preceding process is dissolved.

More specifically, the present invention includes the following [1] to [29].

[1] A method for producing a high-purity ceramide including a process of dissolving a crude ceramide represented by the above-described general formula (1) in a hydrocarbon solvent having 5 to 10 carbon atoms to obtain a hydrocarbon solution and a process of adding an alcohol having 1 to 3 carbon atoms into the hydrocarbon solution to cause crystals to precipitate.

[2] The method for producing a high-purity ceramide described in [1] above, the method further including a process of separating the precipitated crystals and a process of drying the separated crystals.

[3] The method described in [1] or [2] above, wherein the hydrocarbon solution obtained by dissolving the crude ceramide represented by the above-described general formula (1) in the hydrocarbon solvent having 5 to 10 carbon atoms is a reaction mixture obtained by producing a ceramide represented by the above-described general formula (1) by reacting an aminodiol represented by the above-described general formula (2) with a 1 to 5 carbon atoms of alkyl ester of an aliphatic carboxylic acid having 12 to 24 carbon atoms, wherein the aliphatic carboxylic acid optionally has hydroxyl group(s), in a hydrocarbon solvent having 5 to 10 carbon atoms.

[4] The method described in any one of [1] to [3] above, wherein the hydrocarbon solvent having 5 to 10 carbon atoms consists of one or two or more kinds selected from the group consisting of hexane, heptane, octane, and cyclohexane.

[5] The method described in any one of [1] to [4] above, wherein the alcohol having 1 to 3 carbon atoms is methanol or ethanol.

[6] The method described in any one of [1] to [5] above, wherein $R^1$ is an alkyl group having 13 to 17 carbon atoms and $R^2$ is an alkyl group having 15 to 23 carbon atoms which optionally has hydroxyl group(s).

[7] The method described in any one of [1] to [6] above, wherein $R^1$ is an alkyl group having 15 carbon atoms and has a steric structure of a D-erythro form or a (2S,3R)-form.

[8] The method described in any one of [1] to [7] above, wherein $R^2$ is an alkyl group having 17 carbon atoms and both chemical purity and optical purity of a ceramide to be obtained are 95 to 100%.

[9] The method described in any one of [1] to [8] above, wherein the hydrocarbon solvent having 5 to 10 carbon atoms is heptane and the alcohol having 1 to 3 carbon atoms is methanol.

[10] A method for producing a high-purity ceramide, the method including a process of producing a ceramide represented by the above-described general formula (1) by reacting an aminodiol represented by the above-described general formula (2) with a 1 to 5 carbon atoms of alkyl ester of an aliphatic carboxylic acid having 12 to 24 carbon atoms, wherein the aliphatic carboxylic acid optionally has hydroxyl group(s), in a hydrocarbon solvent having 5 to 10 carbon atoms and a process of adding an alcohol having 1 to 3 carbon atoms into the reaction mixture obtained in the preceding process to cause crystals to precipitate.

[11] The method for producing a high-purity ceramide described in [10] above, the method further including a process of separating the precipitated crystals and a process of drying the separated crystals.

[12] The method described in [10] or [11] above, wherein the hydrocarbon solvent having 5 to 10 carbon atoms consists of one or two or more kinds selected from the group consisting of hexane, heptane, octane, and cyclohexane.

[13] The method described in any one of [10] to [12] above, wherein the process of producing a ceramide is carried out with respect to the aminodiol represented by the general formula (2) under the presence of at least a kind of base selected from the group consisting of potassium hydroxide, sodium hydroxide, sodium alkoxide, and potassium alkoxide.

[14] The method described in any one of [10] to [13] above, wherein the process of producing a ceramide is carried out at 50 to 130° C. and the process of adding an alcohol having 1 to 3 carbon atoms to cause crystals to precipitate is carried out in the range of −10 to 40° C.

[15] The method described in any one of [10] to [14] above, wherein the alcohol having 1 to 3 carbon atoms is methanol or ethanol.

[16] The method described in any one of [10] to [15] above, wherein $R^1$ is an alkyl group having 13 to 17 carbon atoms and $R^2$ is an alkyl group having 15 to 23 carbon atoms which optionally has hydroxyl group(s).

[17] The method described in any one of [10] to [16] above, wherein $R^1$ is an alkyl group having 15 carbon atoms and has a steric structure of a D-erythro form or a (2S,3R)-form.

[18] The method described in any one of [10] to [17] above, wherein $R^2$ is an alkyl group having 17 carbon atoms and both chemical purity and optical purity of a ceramide to be obtained are 95 to 100%.

[19] The method described in any one of [10] to [18] above, wherein the hydrocarbon solvent having 5 to 10 carbon atoms is heptane and the alcohol having 1 to 3 carbon atoms is methanol.

[20] A method for producing a ceramide represented by the above-described general formula (1) by reacting an aminodiol represented by the above-described general formula (2) with a 1 to 5 carbon atoms of alkyl ester of an aliphatic carboxylic acid having 12 to 24 carbon atoms, wherein the aliphatic carboxylic acid optionally has hydroxyl group(s), in a hydrocarbon solvent having 5 to 10 carbon atoms.

[21] The method described in [20] above, wherein the hydrocarbon solvent having 5 to 10 carbon atoms consists of one or two or more kinds selected from the group consisting of hexane, heptane, octane, and cyclohexane.

[22] The method described in [20] or [21] above, the reaction is carried out with respect to the aminodiol represented by the general formula (2) under the presence of at least a kind of base selected from the group consisting of potassium hydroxide, sodium hydroxide, sodium alkoxide, and potassium alkoxide.

[23] The method described in any one of [20] to [22] above, wherein the reaction is carried out at 50 to 130° C.

[24] The method described in any one of [20] to [23] above, wherein $R^1$ is an alkyl group having 13 to 17 carbon atoms and $R^2$ is an alkyl group having 15 to 23 carbon atoms which optionally has hydroxyl group(s).

[25] The method described in any one of [20] to [24] above, wherein $R^1$ is an alkyl group having 15 carbon atoms and has a steric structure of a D-erythro form or a (2S,3R)-form.

[26] The method described in any one of [20] to [25] above, wherein $R^2$ is an alkyl group having 17 carbon atoms and both chemical purity and optical purity of a ceramide to be obtained are 95 to 100%.

[27] The method described in any one of [20] to [26] above, wherein the hydrocarbon solvent having 5 to 10 carbon atoms is heptane and the alcohol having 1 to 3 carbon atoms is methanol.

[28] A high-purity ceramide being powdery in a bulk density range of 0.30 g/mL to 0.40 g/mL.

[29] The high-purity ceramide described in [28] above, wherein both chemical purity and optical purity of the high-purity ceramide are 95 to 100%.

Effects of the Invention

According to the method of the present invention, a primary amide derivative can be produced with high yield in such a manner that a fatty acid alkyl ester and sphinganine that is an aminodiol having a primary alcoholic hydroxyl group and a secondary alcoholic hydroxyl group in its molecule are reacted with each other in a hydrocarbon solvent such as heptane under the presence of basic catalyst and then an alcohol to be generated is extracted as needed. Further, according to the method of the present invention, by adding a desired amount of a lower alcohol such as methanol to a reaction system and cooling, it is possible to precipitate a primary amide derivative having high purity at the interface with high yield and thus it is not necessary to repeat a cumbersome procedure at a purifying stage. Moreover, the obtained primary amide derivative can be dried in a simple manner and no used organic solvent remains in crystals.

Therefore, according to the method of the present invention, it is possible to produce a high-purity ceramide which is useful for a cosmetic material or the like in a simple manner and to provide a practical and industrial method for producing a high-purity ceramide.

Further surprisingly, the high-purity ceramide produced by the present method has a lower bulk density than that of a ceramide produced by a method of prior art and even in a case where the high-purity ceramide is added to perfumery cosmetics like cosmetics or a case where the ceramide as in a powdery state is added to a foundation makeup, it is found that the high-purity ceramide can contribute to uniform solubility or improvement of usability in the manufacture of the above-described product group.

DESCRIPTION OF EMBODIMENT $R^1$ in the general formula (1) of the present invention is a residue for forming a sphingoid (a long-chain amino alcohol having 16 to 20 carbon atoms) and is not particularly limited as long as it can form a sphingoid. As preferred $R^1$, an alkyl group having 13 to 17 carbon atoms which optionally has carbon-carbon unsaturated bond(s) is exemplified. The alkyl group having 13 to 17 carbon atoms is a linear or branched alkyl group having 13 to 17 carbon atoms and examples thereof include a tridecyl group, a tetradecyl group, a pentadecyl group, a hexadecyl group, a heptadecyl group, and the like. One or more of the carbon-carbon bonds of these alkyl groups may be an unsaturated bond formed by a carbon-carbon double bond. One to five, preferably one to three, of such unsaturated bonds may be present in the alkyl group. As a preferred alkyl group, a pentadecyl group is exemplified.

$R^2$ in the general formula (1) of the present invention is a residue obtained by excluding a carboxyl group from a fatty acid capable of producing a ceramide, and is not particularly limited as long as it is a residue of fatty acid capable of producing a ceramide. As preferred $R^2$, an alkyl group having 11 to 23 carbon atoms is exemplified and corresponds to a residue obtained by excluding a carboxyl group from a fatty acid having 12 to 24 carbon atoms. As the alkyl group having 11 to 23 carbon atoms, a linear or branched alkyl group having 11 to 23 carbon atoms is exemplified and the alkyl group may have one or more carbon-carbon unsaturated bonds forming a fatty acid. In addition, the alkyl group may have one or more hydroxyl groups and preferably have one hydroxyl group. As a preferred example of the alkyl group having hydroxyl group(s), a 2-hydroxy-alkyl group described in Patent Document 4 or the like is exemplified. As a particularly preferred alkyl group in the present invention, a heptadecanyl group is exemplified.

As an ester residue of ester which is subjected to a reaction with the compound of the general formula (2) of the present invention, it is preferable to use an ester residue having a boiling point at which an alcohol derived from the ester residue generated in an amidation reaction can be separated by distillation at temperature used in the amidation reaction. As a preferred ester residue, a linear or branched alkyl group having 1 to 5 carbon atoms, preferably 1 to 3 carbon atoms, is exemplified. Examples of a particularly preferred alkyl group include a methyl group, an ethyl group, and the like.

The ceramide represented by the general formula (1) of the present invention has two or more asymmetric carbon atoms. Each of these asymmetric carbon atoms may have either the same steric configuration, or a mixture of steric configurations. In a case where the ceramide represented by the general formula (1) of the present invention is used as a material used for a living body like a cosmetic material, it is preferable that the steric configuration be determined. In a case where the ceramide represented by the general formula (1) of the present invention has two asymmetric carbon atoms, there are four kinds of enantiomers. However, any one of these enantiomers may be used or a mixture of these may be used. As a preferred enantiomer, a D-erythro form or a (2S,3R)-form is exemplified.

The crude ceramide that is used as a raw material in the method for producing a high-purity ceramide of the present invention can be produced, for example, by various known methods as disclosed in Patent Documents 1 to 4. In addition, a ceramide obtained from natural substances can be also used. A method for obtaining a crude ceramide for use in the method of the present invention is not particularly limited, but a method for producing a crude ceramide using a hydrocarbon as a solvent according to the method of the present invention is particularly preferable.

As the hydrocarbon solvent having 5 to 10 carbon atoms which is used in the method for producing a high-purity ceramide of the present invention, a linear or branched alkane having 5 to 10 carbon atoms or a monocyclic or bicyclic, preferably monocyclic, cycloalkane having 5 to 10 carbon atoms is exemplified. Examples of the alkane having 5 to 10 carbon atoms include hexane, heptane, octane, nonane, decane, and the like. Examples of the cycloalkane include cyclohexane, methylcyclohexane, and the like. A use amount of the hydrocarbon solvent is not particularly limited as long as it is an amount sufficient for dissolving a crude product of the ceramide represented by the general formula (1). As a preferred use amount, a range of 1 to 10 parts by weight is appropriate per 1 part by mass of the ceramide represented by the general formula (1).

In a case where the ceramide represented by the general formula (1) is dissolved in the hydrocarbon solvent, it is preferable to heat and dissolve the ceramide. As a temperature when the ceramide is dissolved, a temperature can be arbitrarily selected in a range from room temperature or higher to a boiling point of the solvent, but is preferably in a range from 40° C. to a boiling point of the solvent, more preferably in a range from 50° C. to a boiling point of the solvent, and still more preferably in a range from 70° C. to a boiling point of the solvent.

As an alcohol used in the method for producing a high-purity ceramide of the present invention, an aliphatic saturated alcohol having 1 to 5 carbon atoms, preferably 1 to 3 carbon atoms, is exemplified and examples thereof include methanol, ethanol, propanol, and butanol. A use amount of the alcohol solvent is typically 50 parts by mass or less, preferably 0.5 to 50 parts by mass, and more preferably 1 to 20 parts by mass, per 1 part by mass of the hydrocarbon solvent having 5 to 10 carbon atoms. A time point at which the alcohol is added is not particularly limited as long as it is a time point after the ceramide represented by the general formula (1) is dissolved completely. However, adding is carried out preferably before precipitation of crystals is started, and adding is started in a state where a temperature of the solution is 30° C. or higher, and preferably 40° C. or higher.

A temperature at which to cause crystals to precipitate in the presence of added alcohol is in a range of −20° C. to room temperature, preferably in a range of −20° C. to +20° C., and more preferably in a range of 5° C. to +20° C. The crystals precipitated in such a manner can be separated through filtration or the like and the separated crystals can be further dried and then purified. The drying is preferably carried out in vacuo.

A preferred aspect of the method for producing a high-purity ceramide of the present invention is, for example, a method including the following processes:

(1) a process of heating and dissolving a crude ceramide in a hydrocarbon solvent;

(2) a process of adding an alcohol to the obtained hydrocarbon solution of the crude ceramide; and (3) a process of cooling in the range of −20° C. to +20° C. to cause crystals to precipitate, and preferably, the method further including the following processes:

(4) a process of separating the precipitated crystals through filtration; and (5) a process of drying the separated crystals.

The optically active aminodiol represented by the general formula (2) that is a raw material used in the method for producing a ceramide using a hydrocarbon as a solvent of the present invention can be produced, for example, by a method illustrated by the following Scheme 1.

The method illustrated by Scheme 1 will be described. First, (i) the α position of β-keto ester is converted into a nitrogen-containing group such as an imino group and an oxime group and then is subjected to reduction or the like to produce an intermediate compound (A). Subsequently, (ii) a keto group is selectively subjected to asymmetric hydrogenation to produce a compound (B), (iii) the reduction of an ester group is carried out using a reducing agent such as sodium borohydride, and then (iv) deacetylation is carried out. Therefore, the optically active aminodiol can be produced. Moreover, by performing inversion reaction of the hydroxyl group derived from the keto group of the β position, conversion into a compound with a hydroxyl group of desired steric configuration can be carried out.

[Chemical Formula 3]

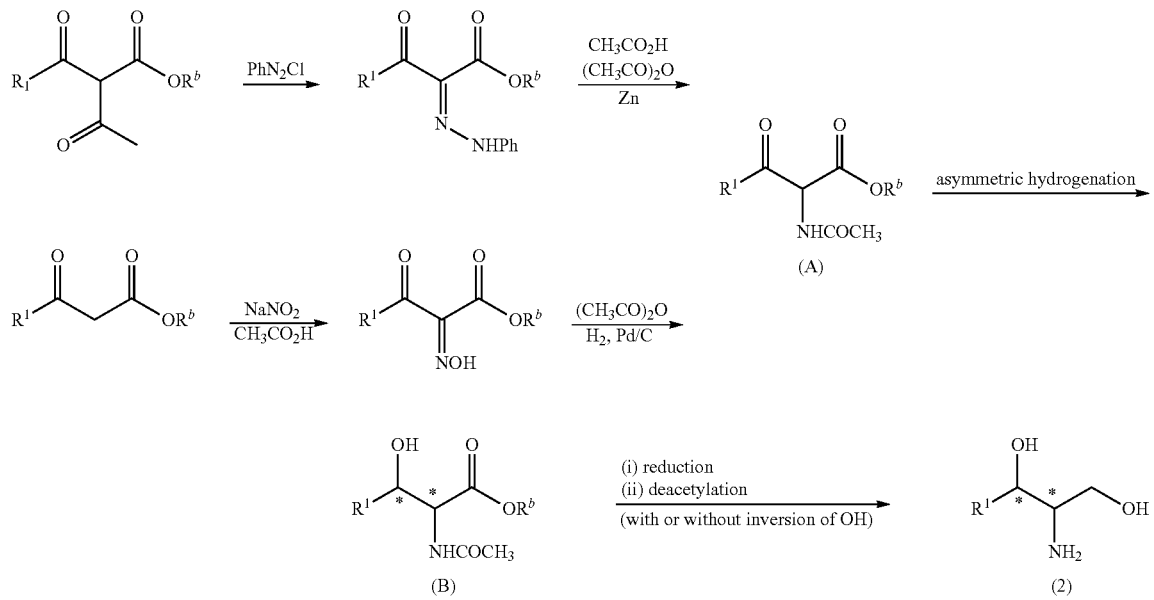

(In the formula, $R^b$ represents an ester residue such as an alkyl group; and $R^1$ has the same meaning as described above.)

That is, the compound (A) can be produced, for example, by a two-step reaction using β-keto ester as a raw material according to methods described in Shapiro et al., J. Am. Chem. Soc., 80, 2170 (1958), and G. I. Gregory et al., J. Chem. Soc., 2453 (1951), or the like.

In addition, the compound (B) can be produced, for example, in such a manner that the compound (A) that is a starting material is subjected to asymmetric hydrogenation in a solvent under the presence of a ruthenium complex. As the solvent, a protic solvent such as methanol, ethanol, and isopropyl alcohol is preferable. Alternatively, a mixed solvent of the protic solvent and tetrahydrofuran, toluene, hexane, heptane, methyl acetate, ethyl acetate, methylene chloride, chloroform, or the like is preferable. In particular, a mixed solvent of methylene chloride and the protic solvent, such as methanol, ethanol, and isopropyl alcohol, is more preferable. It is preferable that the compound (A) be subjected to an asymmetric hydrogenation reaction after the compound (A) is dissolved in above-described solvent.

If the ruthenium complex used in the reaction is added in an amount of 1/100 to 1/100000 fold mol, and more preferably 1/200 to 1/10000 fold mol with respect to the compound (A), the asymmetric hydrogenation reaction is preferably advanced.

The asymmetric hydrogenation reaction can be carried out in such a manner that a hydrogen pressure is set to 0.1 to 10 MPa and more preferably 1 to 5 MPa, a reaction temperature is set to 0 to 150° C. and preferably 20 to 100° C., and stirring is carried out for 1 to 48 hours. The optically active compound (B) of the syn-form thus obtained can be converted into the optically active compound (B) of the anti-form by inverting the steric configuration of β-positioned hydroxyl group if necessary. As the ruthenium complex preferably used in the asymmetric hydrogenation reaction, the following complexes are exemplified.

[Ru$_2$Cl$_4$(SEGPHOS)$_2$](NEt$_3$) (SEGPHOS represents [4,4'-bis-1,3-benzodioxole]-5,5'-diylbis(diphenylphosphine)), [Ru$_2$Cl$_4$(p-Tol-SEGPHOS)$_2$](NEt$_3$) (p-Tol-SEGPHOS represents [4,4'-bis-1,3-benzodioxole]-5,5'-diylbis[di-p-tolylphosphine]), [Ru$_2$Cl$_4$(DM-SEGPHOS)$_2$](NEt$_3$) (DM-SEGPHOS represents [4,4'-bis-1,3-benzodioxole]-5,5'-diylbis[di-3,5-dimethylphenylphosphine]), [RuCl(benzene)(SEGPHOS)]Cl, [RuBr(benzene)(SEGPHOS)]Br, [RuI(benzene)(SEGPHOS)]I, [RuCl(p-cymene)(SEGPHOS)]Cl, [RuBr(p-cymene)(SEGPHOS)]Br, [RuI(p-cymene)(SEGPHOS)]I, [RuCl(benzene)(p-Tol-SEGPHOS)]Cl, [RuBr(benzene)(p-Tol-SEGPHOS)]Br, [RuI(benzene)(p-Tol-SEGPHOS)]I, [RuCl(p-cymene)(p-Tol-SEGPHOS)]Cl, [RuBr(p-cymene)(p-Tol-SEGPHOS)]Br, [RuI(p-cymene)(p-Tol-SEGPHOS)]I, [RuCl(benzene)(DM-SEGPHOS)]Cl, [RuBr(benzene)(DM-SEGPHOS)]Br, [RuI(benzene)(DM-SEGPHOS)]I, [RuCl(p-cymene)(DM-SEGPHOS)]Cl, [RuBr(p-cymene)(DM-SEGPHOS)]Br, [RuI(p-cymene)(DM-SEGPHOS)]I, [Ru(OAc)$_2$(SEGPHOS)] (OAc represents an acetoxy group), [Ru(OAc)$_2$(p-Tol-SEGPHOS)], [Ru(OAc)$_2$(DM-SEGPHOS)], [RuBr$_2$(SEGPHOS)], [RuBr$_2$(p-Tol-SEGPHOS)], [RuBr$_2$(DM-SEGPHOS)], [Ru(SEGPHOS)](BF$_4$)$_2$, [Ru(SEGPHOS)](ClO$_4$)$_2$, [Ru(SEGPHOS)](PF$_6$)$_2$, [Ru(p-Tol-SEGPHOS)](BF$_4$)$_2$, [Ru(p-Tol-SEGPHOS)](ClO$_4$)$_2$, [Ru(p-Tol-SEGPHOS)](PF$_6$)$_2$, [Ru(DM-SEGPHOS)](BF$_4$)$_2$, [Ru(DM-SEGPHOS)](ClO$_4$)$_2$, [Ru(DM-SEGPHOS)](PF$_6$)$_2$, [{RuCl(SEGPHOS)}$_2$(μ-Cl)$_3$][NH$_2$Me$_2$], [{RuCl(SEGPHOS)}$_2$(μ-Cl)$_3$][NH$_2$Et$_2$], [{RuCl(p-Tol-SEGPHOS)}$_2$(μ-Cl)$_3$][NH$_2$Me$_2$], [{RuCl (p-Tol-SEGPHOS)}$_2$(μ-Cl)$_3$][NH$_2$Et$_2$], [{RuCl(DM-SEGPHOS)}$_2$(μ-Cl)$_3$][NH$_2$Me$_2$], [{RuCl(DM-SEGPHOS)}$_2$(μ-Cl)$_3$][NH$_2$Et$_2$], RuCl$_2$(SEGPHOS) (DMF)n, RuCl$_2$(p-Tol-SEGPHOS) (DMF)n, and RuCl$_2$(DM-SEGPHOS) (DMF)n.

These complexes can be produced by a method described in U.S. Pat. Nos. 5,872,273 or 6,313,317, and also a commercialized product is available.

Moreover, these complexes can be synthesized by an asymmetric hydrogen transfer reaction of the compound (A) according to the method described in U.S. Pat. No. 8,207,370. In other words, the compound (A) is asymmetrically reduced using an optically active amine complex as a catalyst and thus the optically active compound (B) of the anti-form can be produced directly.

The β-positioned hydroxyl group of the compound (B) is subjected to intramolecular inversion using thionyl chloride by a general method if necessary. Subsequently, the ester moiety is reduced using a reducing agent such as lithium borohydride and lithium aluminum hydride and then the amide group is hydrolyzed using a hydrochloric acid or the like. Thereafter, an optically active target compound (C) can be obtained.

The amidation of the amino group is carried out by reacting a 1 to 5 carbon atoms of alkyl ester of a carboxylic acid having 12 to 24 carbon atoms, wherein the carboxylic acid optionally has hydroxyl group(s), wherein the 1 to 5 carbon atoms of alkyl ester is preferably a methyl or ethyl ester, with the obtained aminodiol derivative represented by the general formula (2). Therefore, the ceramide represented by the general formula (1) can be produced.

Examples of the hydrocarbon solvent having 5 to 10 carbon atoms which is used in the process of amidation include a linear or branched alkane having 5 to 10 carbon atoms and a monocyclic or bicyclic, preferably monocyclic, cycloalkane having 5 to 10 carbon atoms. Examples of the alkane having 5 to 10 carbon atoms include hexane, heptane, octane, nonane, decane, and the like. Examples of the cycloalkane include cyclohexane, methylcyclohexan, and the like. A use amount of the hydrocarbon solvent is appropriate in a range of 1 to 10 parts by weight per 1 part by weight of the aminodiol derivative represented by the general formula (2).

In the process of amidation, a basic compound can be used as a catalyst and examples of the basic compound which is used include an alkali metal hydroxide such as potassium hydroxide and sodium hydroxide, an alkali metal alkoxide such as sodium methoxide, potassium methoxide, sodium ethoxide, and potassium t-butoxide, and the like.

The amidation can be carried out at a reaction temperature of 30° C. to 150° C. and preferably 50° C. to 130° C., and for a reaction time of one hour to 10 hours.

Upon the completion of amidation reaction, an alcohol having 1 to 5 carbon atoms, and preferably 1 to 3 carbon atoms, can be added directly to a reaction mixture. The processes from adding an alcohol to separating and drying the ceramide represented by the general formula (1) can be carried out under the same condition as the condition in the above-described method for producing a high-purity ceramide.

In the method for producing a high-purity ceramide of the present invention subsequently to the amidation reaction of the present invention using a hydrocarbon solvent, a high-purity ceramide can be produced directly from a reaction mixture of amidation. Therefore, this method is particularly preferable. According to the method, it is possible to easily produce a high-purity ceramide by a two-step reaction of amidation and crystallization and thus this method is particularly suitable for industrialization.

EXAMPLES

Hereinafter, the present invention will be described in detail with reference to Examples, but it is not intended that the present invention is limited thereto.

Incidentally, an analytical instrument or an analytical means to be described below is employed.

(Analytical Instrument and Condition)
High-performance liquid chromatograph: Waters 510 (manufactured by Waters)
Detector: UV Detector Waters 484 (manufactured by Waters)
Detector: RI Detector Waters 2414 (manufactured by Waters)
Nuclear magnetic resonance spectrometer: AM-400 Type Device, 400 MHz (manufactured by Bruker Inc.)
Internal standard material: Tetramethylsilane
Optical rotation polarimeter: DIP-4 Type Device (maunfactured by Nippon Bunko Kogyo Co., Ltd.)
Elemental analyzer: CHN-2400 (manufactured by Perkin Elmer)
Mass spectrometer: M80B (manufactured by Hitachi, Ltd.)

Synthesis Example 1

The asymmetric reduction of an α-amino-β-keto ester derivative was carried out according to the reaction formula to be described below.

[Chemical Formula 4]

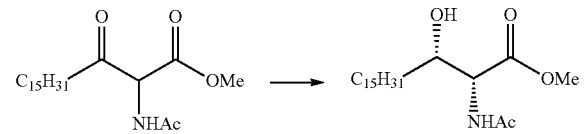

To a 500 ml autoclave made of hastelloy, 50 g (0.135 mol) of 2-N-acetamide-hexadecanoyl acetic acid methyl ester (hereinafter, referred to as the compound (C) in some cases), were added 370 mg (0.45 mmol) of [{RuCl((S)-(−)-SEGPHOS)}$_2$(µ-Cl)$_3$][Me$_2$NH$_2$], and 250 ml of a mixture solvent of CH$_2$Cl$_2$:MeOH=10:1 and the mixture was subjected to a reaction with stirring at a hydrogen pressure of 2.4 MPa and a temperature of 80° C. for 20 hours. The reaction mixture was cooled down to room temperature. The enantiomeric excess of the reaction mixture was measured using HPLC (column: CHIRALCEL OD-H, eluent: Hexane/EtOH=95/5 (v/v), flow rate: 0.5 ml/min, detection wavelength: UV-210 nm) and the diastereo selectivity thereof was measured using HPLC (column: Inertsil ODS-3V, eluent: methanol/water=90/10 (v/v), flow rate: 1.5 ml/min, column temperature: 40° C., detection: RI). As a result, the enantiomeric excess was 99% e.e., and the diastereo selectivity was 95.5% d.e. (syn/anti-form diastereomeric excess (%)). After the completion of reaction, the solvent was recovered and crystals were separated by using the mixture of ethyl acetate and hexane and dried. Therefore, 47.8 g (yield: 95.3%) of (2R,3S)-2-N-acetamide-3-hydroxy octadecanoic acid methyl ester (hereinafter, referred to as a compound (D) in some cases) was obtained.

Synthesis Example 2

The asymmetric reduction was carried out according to the reaction formula to be described below in the same manner as in Synthesis Example 1.

[Chemical Formula 5]

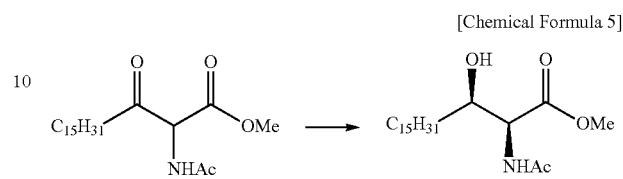

The yield 96.7% of (2S,3R)-2-N-acetamide-3-hydroxy octadecanoic acid methyl ester was obtained in the same manner as in Synthesis Example 1, except that [{RuCl((R)-(−)-DM-SEGPHOS)}$_2$(µ-Cl)$_3$][Me$_2$NH$_2$] was used as a catalyst in an amount of 1/1000 fold mol with respect to the compound (C). The enantiomeric excess was 99% e.e, and the diastereo selectivity was 95.8% d.e.

Synthesis Example 3

An acetyl group that is a protective group of an amino group was hydrolyzed according to the reaction formula to be described below.

[Chemical Formula 6]

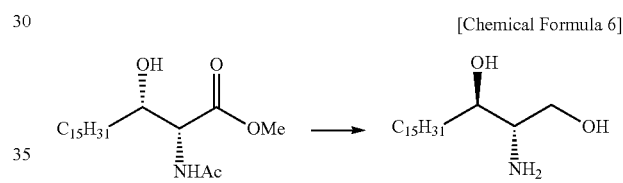

The (2R,3S)-2-N-acetamide-3-hydroxy octadecanoic acid methyl ester (47.8 g) obtained in Synthesis Example 1 was reacted with thionyl chloride such that the steric configuration of the hydroxyl group was inverted and thus was converted into a (2R,3R)-form. Thereafter, the ester moiety was reduced by sodium borohydride. Furthermore, the acetyl group was hydrolyzed to obtain (2S,3R)-2-amino octadecane-1,3-diol (40.1 g) (hereinafter, referred to as a compound (E) in some cases) (chemical purity 90%, 95% d.e.).

Example 1

The amidation of the amino group was carried out according to the reaction formula to be described below.

[Chemical Formula 7]

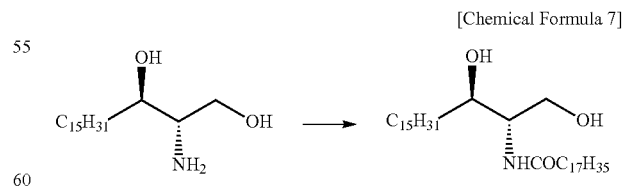

A 1 L four-neck flask equipped with a water draining device and a Dimroth condenser was loaded with 500 ml of heptane and 1.20 g of 28% sodium methoxide solution with respect to 40.1 g of the compound (E) obtained in Synthesis Example 3, and was heated at a bath temperature of 110° C. under stirring.

38.85 g of methyl stearate which has been dissolved in 100 ml of heptane in advance was added dropwise thereto over about one hour and the reaction was completed within one hour at the same temperature while methanol was separated from the heptane layer and then distilled out. After the completion of the reaction, when 200 ml of methanol was gradually added dropwise and then cooled down as is, a ceramide ((2S,3R)-2-octadecanoyl amino octadecane-1,3-diol) was started to be precipitated at around 43° C. and then the cooling was continued as is to be cooled down to 10° C. under stirring. The filtration was carried out at about 10° C. to separate crystals and the separated crystals were washed with 100 ml of ethanol of 10° C. Then, powdery crystals (64.8 g) were obtained. The obtained powder was dried in vacuo (40 to 50° C./20 to 5 mmHg) to obtain 59.14 g of ceramide (the yield from the compound (D) was 80.9%) as white powder (the solvent residual amount was 8.7%). The chemical purity of the obtained ceramide powder was 99% or more and the optical purity thereof was also 99% d.e. or more.

Comparative Example 1

The same reaction was carried out by using 1-butanol instead of the heptane of Example 1, and a ceramide was separated at 90° C. and washed with 100 ml of methanol. Therefore, solvent-containing powder (94.8 g) was obtained. The obtained powder was dried under the same condition as in Example 1 to obtain 48.7 g of ceramide (the yield from the compound (D) was 66.7%).
The chemical purity was 95.5% and the optical purity was 97.2% d.e., but the yield was lower than that of Example 1. Moreover, butanol odor remained in the obtained powder and it was found from the weight reduction rate before and after drying that the solvent residual amount was high, that is, 47.5%.

Example 2

A high-purity ceramide was produced from (2S,3R)-2-octadecanoyl amino octadecane-1,3-diol (a crude ceramide) having a chemical purity of 89% and an optical purity of 90% d.e. using each solvent presented in the following Table 1. After heating and dissolving the crude ceramide in the hydrocarbon solvent in an amount of 20 fold volume with respect to 1 part by mass of crude ceramide, an alcohol having a ratio presented in Table 1 was added and the mixture was cooled down to a temperature presented in Table 1 to cause crystals to precipitate. The crystals were separated and dried and then a separation state, an amount (yield) thereof, and purity were measured.
The results are presented in Table 1.

TABLE 1

| run | Solvent | Separation temperature | Separation state | Yield % | de % |
|---|---|---|---|---|---|
| 1 | Heptane/EtOH = 4/1 | 10° C. | Excellent | 92.0 | 97.4 |
| 2 | Heptane/EtOH = 3/1 | 10° C. | Excellent | 91.3 | 98.7 |
| 3 | Heptane/EtOH = 2/1 | 6–8° C. | Excellent | 87.0 | 99.5 or more |
| 4 | Heptane/MeOH = 3/1 | 20° C. | Excellent | 84.8 | 99.5 or more |
| 5 | Hexane/MeOH = 4/1 | 10° C. | Excellent | 86.8 | 98.9 |
| 6 | EtOH | 20° C. | Good | 90.0 | 92.9 |
| 7 | BuOH | 60° C. | Poor: solidified (inseparable) | — | — |

The bulk densities of powders obtained in run 1 to run 5 were 0.38 g/ml, 0.36 g/ml, 0.35 g/ml, 0.34 g/ml, and 0.37 g/ml, respectively, and all chemical purities thereof were 98% or more. On the other hand, the bulk density of powder obtained in run 6 was 0.43 g/ml and the chemical purity thereof was 94.2%.

The invention claimed is:
1. A method for producing a high-purity ceramide, the method comprising:
 a process of producing a ceramide represented by the following general formula (1) by reacting an aminodiol represented by the following general formula (2) with a 1 to 5 carbon atoms of alkyl ester of an aliphatic carboxylic acid having 12 to 24 carbon atoms, wherein the aliphatic carboxylic acid optionally has hydroxyl group(s), in a hydrocarbon solvent having 5 to 10 carbon atoms; and
 a process of adding an alcohol having 1 to 3 carbon atoms into the reaction mixture obtained in the preceding process to cause crystals to precipitate,

[Chemical Formula 1]

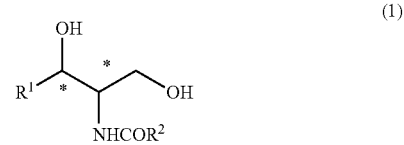

(1)

(wherein $R^1$ represents an alkyl group having 13 to 17 carbon atoms which optionally has carbon-carbon unsaturated bond(s); $R^2$ represents an alkyl group having 11 to 23 carbon atoms which optionally has hydroxyl group(s); and * indicates an optically active center)

[Chemical Formula 2]

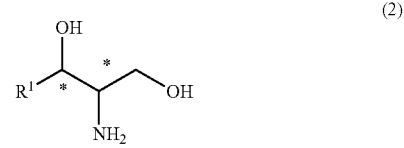

(2)

(wherein $R^1$ represents an alkyl group having 13 to 17 carbon atoms which optionally has carbon-carbon unsaturated bond(s); and * indicates an optically active center).

2. The method for producing a high-purity ceramide according to claim 1, the method further comprising:
 a process of separating the precipitated crystals; and
 a process of drying the separated crystals.
3. The method according to claim 1, wherein the hydrocarbon solvent having 5 to 10 carbon atoms consists of one or two or more kinds selected from the group consisting of hexane, heptane, octane, and cyclohexane.

4. The method according to claim 1, wherein the process of producing a ceramide is carried out with respect to the aminodiol represented by the general formula (2) under the presence of at least a kind of base selected from the group consisting of potassium hydroxide, sodium hydroxide, sodium alkoxide, and potassium alkoxide.

5. The method according to claim 1, wherein the process of producing a ceramide is carried out at 50 to 130° C. and the process of adding an alcohol having 1 to 3 carbon atoms to cause crystals to precipitate is carried out in a range of −10 to 40° C.

6. The method according to claim 1, wherein the alcohol having 1 to 3 carbon atoms is methanol or ethanol.

7. The method according to claim 1, wherein $R^1$ is an alkyl group having 13 to 17 carbon atoms and $R^2$ is an alkyl group having 15 to 23 carbon atoms which optionally has hydroxyl group(s).

8. The method according to claim 1, wherein $R^1$ is an alkyl group having 15 carbon atoms and has a steric structure of a D-erythro form or a (2S,3R)- form.

9. The method according to claim 1, wherein $R^2$ is an alkyl group having 17 carbon atoms and both chemical purity and optical purity of a ceramide to be obtained are 95 to 100%.

10. The method according to claim 1, wherein the hydrocarbon solvent having 5 to 10 carbon atoms is heptane and the alcohol having 1 to 3 carbon atoms is methanol.

11. A high-purity ceramide being powdery in a bulk density range of 0.30 g/mL to 0.40 g/mL.

12. The high-purity ceramide according to claim 11, wherein both chemical purity and optical purity of the high-purity ceramide are 95 to 100%.

* * * * *